(12) United States Patent
Gyollai et al.

(10) Patent No.: US 7,279,571 B2
(45) Date of Patent: Oct. 9, 2007

(54) METHODS OF PREPARING PIMECROLIMUS

(75) Inventors: Viktor Gyollai, Debrecen (HU); Csaba Szabo, Debrecen (HU)

(73) Assignee: TEVA Gyógyszergyár Zártkörüen Müködö Részvénytársaság, Debrecen (HU)

( * ) Notice: Subject to any disclaimer, the term of this patent is extended or adjusted under 35 U.S.C. 154(b) by 0 days.

(21) Appl. No.: 11/293,353

(22) Filed: Dec. 1, 2005

(65) Prior Publication Data

US 2006/0142564 A1      Jun. 29, 2006

Related U.S. Application Data

(60) Provisional application No. 60/709,160, filed on Aug. 17, 2005, provisional application No. 60/705,681, filed on Aug. 3, 2005, provisional application No. 60/662,440, filed on Mar. 16, 2005, provisional application No. 60/641,869, filed on Jan. 5, 2005, provisional application No. 60/641,868, filed on Jan. 5, 2005, provisional application No. 60/641,697, filed on Jan. 5, 2005, provisional application No. 60/633,926, filed on Dec. 6, 2004, provisional application No. 60/632,372, filed on Dec. 1, 2004.

(51) Int. Cl.
*C07D 498/18* (2006.01)

(52) U.S. Cl. .................................... 540/456
(58) Field of Classification Search .............. 540/456; 514/291
See application file for complete search history.

(56) References Cited

U.S. PATENT DOCUMENTS

| | | |
|---|---|---|
| 3,244,592 A | 4/1966 | Arai et al. |
| 6,423,722 B1 | 7/2002 | Dosenbach et al. |
| 6,620,325 B2 | 9/2003 | Fuenfschilling et al. |
| 6,706,727 B1 | 3/2004 | Fleissner et al. |

FOREIGN PATENT DOCUMENTS

| | | |
|---|---|---|
| EP | 0 323 865 A1 | 7/1989 |
| EP | 0 427 680 A1 | 5/1991 |
| EP | 0 480 623 A1 | 4/1992 |
| EP | 1 234 833 A2 | 8/2002 |
| WO | WO 93/04679 A1 | 3/1993 |
| WO | WO 93/18050 A1 | 9/1993 |
| WO | WO 03/063821 A2 | 8/2003 |
| WO | WO 03/063822 A2 | 8/2003 |
| WO | WO 2004/089958 A2 | 10/2004 |
| WO | WO 2005/010015 A1 | 2/2005 |
| WO | WO 2005/117837 A1 | 12/2005 |
| WO | WO 2006/031664 A1 | 3/2006 |

OTHER PUBLICATIONS

Griffiths, C.E., "Ascomycin: An Advance in the Management of Atopic Dermatitis." *British Journal of Dermatology*, (2001) vol. 144, p. 679-681.

Kessler, H., et al., "Structure of Rapamycin: An NMR and Molecular-Dynamics Investigation" Helvetica Chimica Acta, (1993)vol. 76, p. 117-130.

Brittain, H.G. (Editor) "Polymorphism in Pharmaceutical Solids" Drugs and the Pharmaceutical Sciences vol. 95, (1999) Marcel Dekker, Inc. New York, New York.

Remington, J. P. (Editor) "The Science and Practice of Pharmacy", vol. II, Chapter 92, "Oral Solid Dosage Forms", p. 1615-1649 (1995) Mack Publishing Company, Easton, Pennsylvania.

Yu, L: "Amorphous Pharmaceutical Solids: Preparation, Characterization and Stabilization." Advanced Drug Delivery Reviews, (2001) vol. 48, p. 27-42.

*Primary Examiner*—Bruck Kifle
(74) *Attorney, Agent, or Firm*—Kenyon & Kenyon LLP

(57) ABSTRACT

The present invention provides a process for the preparation of pimecrolimus from ascomycin in which ascomycin is reacted with a conversion reagent that converts ascomycin to its activated derivative at C-32. The activated ascomycin is then reacted with chloride ion. The process of the invention requires fewer process steps than prior art processes, and does not require the protection of the ascomycin C-24 hydroxyl group or the purification of the activated ascomycin derivative.

28 Claims, 1 Drawing Sheet

Pimecrolimus impurity profile

Area Percent Report

| Peak # | RetTime [min] | Type | Width [min] | Area [mAU*s] | Area % | Name |
|---|---|---|---|---|---|---|
| 1 | 6.024 | VV | 0.1787 | 34.53588 | 0.1789 | ? |
| 2 | 6.382 | VV | 0.6103 | 123.29395 | 0.6388 | ? |
| 3 | 7.133 | VV | 0.3509 | 58.16304 | 0.3014 | ? |
| 4 | 7.666 | VV | 0.4208 | 47.18306 | 0.2445 | ? |
| 5 | 7.946 |  | 0.0000 | 0.00000 | 0.0000 | Ascomycin |
| 6 | 8.371 | VBA | 0.2334 | 8.66038 | 0.0449 | ? |
| 7 | 9.165 | BV | 0.2487 | 31.91078 | 0.1653 | ? |
| 8 | 9.703 | VBA | 0.1953 | 1.90801 | 9.886e-3 | ? |
| 9 | 12.283 | BV | 0.2562 | 5.51753 | 0.0286 | ? |
| 10 | 13.471 | BV | 0.3505 | 3.28971 | 0.0170 | ? |
| 11 | 14.198 | VV | 0.4242 | 6.62931 | 0.0343 | ? |
| 12 | 14.891 | VBA | 0.4618 | 5.67820 | 0.0294 | ? |
| 13 | 18.039 | BP | 0.4111 | 8.28581 | 0.0429 | ? |
| 14 | 19.255 | VV | 0.4787 | 30.91410 | 0.1602 | Tautomer II |
| 15 | 20.082 | VV | 0.3876 | 17.69263 | 0.0917 | ? |
| 16 | 20.513 | VP | 0.5683 | 56.33489 | 0.2919 | RRt=0.84 |
| 17 | 22.570 | PP | 0.3309 | 6.96077 | 0.0361 | ? |
| 18 | 23.274 | VP | 0.3387 | 7.74057 | 0.0401 | ? |
| 19 | 26.169 | BV | 0.8001 | 1.84806e4 | 95.7532 | Pimecrolimus |
| 20 | 28.475 | VBA | 0.7767 | 103.08733 | 0.5341 | ? |
| 21 | 32.655 | BV | 0.4634 | 33.75341 | 0.1749 | ? |
| 22 | 32.816 | VV | 0.4531 | 44.18368 | 0.2289 | ? |

METHODS OF PREPARING PIMECROLIMUS

RELATED APPLICATIONS

This application claims benefit of U.S. Provisional Patent Applications Nos. 60/632,372, filed Dec. 1, 2004, 60/633,926, filed Dec. 6, 2004, 60/641,697, filed Jan. 5, 2005, 60/641,868, filed Jan. 5, 2005, 60/641,869, filed Jan. 5, 2005, 60/662,440, filed Mar. 16, 2005, 60/705,681, filed Aug. 3, 2005, and 60/709,160, filed Aug. 17, 2005, the contents of which are incorporated herein in their entirety by reference.

FIELD OF THE INVENTION

The present invention relates to methods of preparing the anti-inflammatory compound pimecrolimus and to pure pimecrolimus.

BACKGROUND OF THE INVENTION

Pimecrolimus is an anti-inflammatory compound derived from the macrolactam natural product ascomycin, produced by certain strains of Streptomyces. Pimecrolimus is sold in the United States under the brand name ELIDEL®, and is approved for the treatment of atopic dermatitis. The systematic name of pimecrolimus is (1R,9S,12S,13R,14S,17R,18E, 21S,23S,24R,25S,27R)-12-[(1E)-2-{(1R,3R,4S)-4-chloro-3-methoxycyclohexyl}-1-methylvinyl ]-17-ethyl-1,14-dihydroxy-23,25-dimethoxy-13,19,21,27-tetramethyl-11, 28-dioxa-4-aza-tricyclo[22.3.1.0$^{4,9}$]octacos-18-ene-2,3,10, 16-tetraone. Pimecrolimus is the 32-epichloro derivative of ascomycin. Its empirical formula is $C_{43}H_{68}ClNO_{11}$ and its molecular weight is 810.47.

European Patent EP 427 680 B1 discloses a method of synthesizing pimecrolimus in the form of a colorless foamy resin. The disclosed method comprises the following four reaction steps:

(a) protection of the two hydroxyl groups at C-24 and C-32 with t-butyldimethylsilyl ethers;
(b) deprotection of the silyl-protected hydroxyl group at C-32, while the hydroxyl group at C-24 remains protected;
(c) substitution of chlorine for the free hydroxyl group at C-32 with an inversion of configuration; and
(d) deprotection of the silyl-protected hydroxyl group at C-24.

EP 427 680 does not disclose the yield of each step in the synthesis, but does disclose that each step is followed by the chromatographic purification of the product of that step. Accordingly, it would be expected that the overall yield of the process disclosed in EP 427 680 is low, given the number of reaction steps and chromatographic purifications required.

Therefore, a process for the preparation of pimecrolimus having a reduced number of steps, particularly chromatographic steps, would be advantageous. The present invention provides such processes.

SUMMARY OF THE INVENTION

The present invention provides methods for the synthesis of pimecrolimus, comprising dissolving ascomycin in an organic solvent, combining the solution of ascomycin with a base to obtain a reaction mixture, combining the reaction mixture with a conversion reagent to obtain an activated ascomycin derivative, combining the activated derivative of ascomycin with a chloride ion source until obtaining pimecrolimus, and recovering the pimecrolimus.

Preferably, the pimecrolimus obtained by the above process is purified by column chromatography.

Preferably, the purified pimecrolimus has a purity of at least about 95% area by HPLC, more preferably of at least about 98% area by HPLC.

The present invention also provides pimecrolimus having a purity of at least about 95% area by HPLC, more preferably of at least about 98% area by HPLC.

In another embodiment the present invention provides a pharmaceutical formulation comprising a therapeutically effective amount of the above pure pimecrolimus.

In another embodiment the present invention provides a method for treating a patient suffering from atopic dermatitis, comprising the step of administering to the patient the pharmaceutical formulation described above.

DETAILED DESCRIPTION OF THE INVENTION

Figure 1:
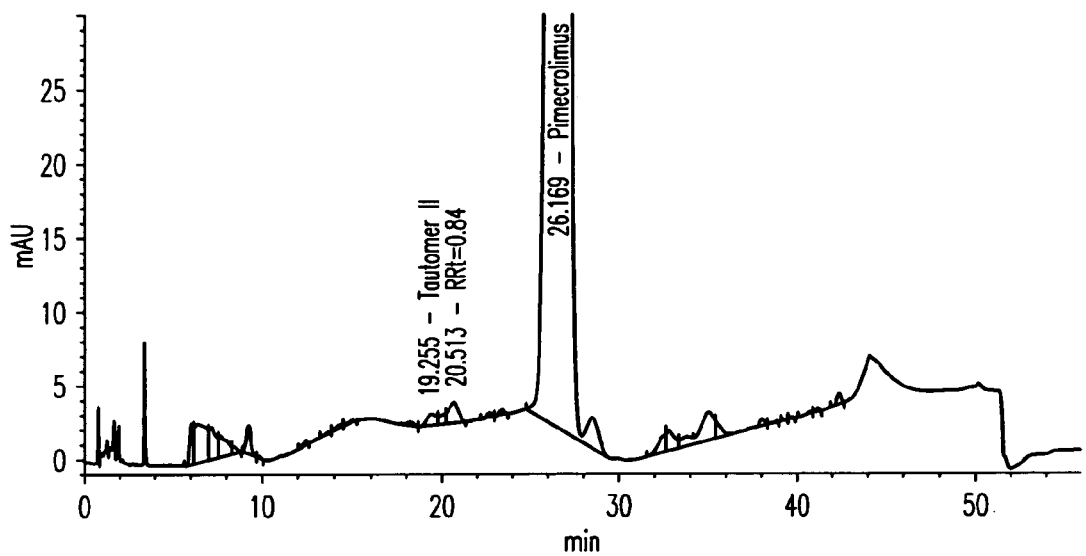
FIG. 1: A chromogram of the pimecrolimus.

The present invention provides methods for the synthesis of pimecrolimus, comprising dissolving ascomycin in an organic solvent, combining the solution of ascomycin with a base to obtain a reaction mixture, combining the reaction mixture with a conversion reagent to obtain an activated ascomycin derivative, combining the activated derivative of ascomycin with a chloride ion source until obtaining pimecrolimus, and recovering the crude pimecrolimus. Optionally, the hydroxyl group at position C-24 of ascomycin is not protected during the process. Contrary to the procedure described in EP 427 680, the selective protection of the hydroxyl group of ascomycin at C-24 is not necessary, since the hydroxyl group at C-32 is activated regioselectively (hydroxyl group at C-24 remains intact). The conversion reagent converts ascomycin to an activated ascomycin derivative at C-32.

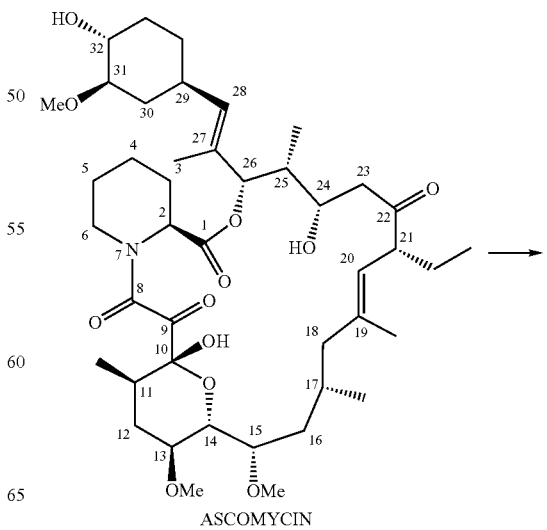

ASCOMYCIN

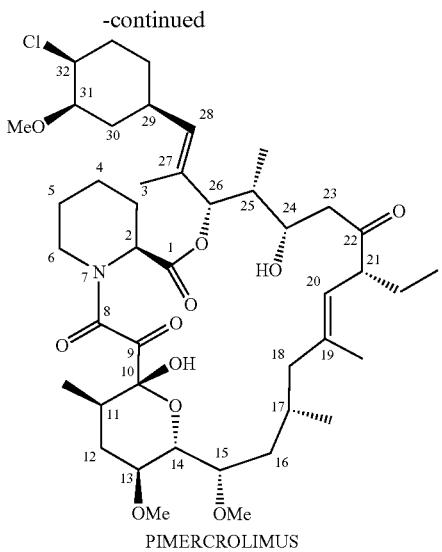

PIMERCROLIMUS

Preferably, the activated ascomycin derivative is a sulfonate ester, more preferably, a tosylate or mesylate, and, most preferably, a triflate.

Preferably, the organic solvent is selected from the group consisting of: dichloromethane, chloroform, diethylether, diisopropylether, methyl-t-butylether, toluene, ethyl acetate, i-butylacetate, acetone, methylethylketone, acetonitrile, N,N-dimethylformamide, N,N-dimethylacetamide, dimethylsulfoxide, and mixtures thereof. More preferably, the organic solvent is toluene or acetonitrile. Preferably, the ascomycin is dissolved in the organic solvent at a temperature of more than about 25° C. The resulting ascomycin solution is then stirred under an inert atmosphere, e.g., nitrogen, at a low temperature of less than about 25° C., preferably, less than about 0° C., and, more preferably, less than about −20° C. The low temperature is necessary for selective reaction and for obtaining low level of side products. The stirring is preferably continued for a time sufficient to dissolve substantially all the ascomycin.

Preferably, the base is in an amount of about 1 to about 4 equivalents. The base can be added dropwise, in parts, or all at once. The base may be an organic or inorganic base. Preferably, the base is selected from the group consisting of triethylamine, diisopropyl-ethylamine (EDIPA), N-methylmorpholine, N,N-dimethylaniline, pyridine, and substituted pyridine derivatives, such as 2,6-lutidine, s-collidine, and 4-dimethylaminopyridine. More preferably, the base is selected from the group consisting of: diisopropyl-ethylamine (EDIPA), s-collidine and 2,6-lutidine. The base may also be added to the ascomycin solution together with the activating conversion reagent in the following step, as described below. The added base may be in solution, where the solvent is preferably selected from the group consisting of: dichloromethane, chloroform, diethylether, diisopropylether, methyl-t-butylether, toluene, ethyl acetate, i-butylacetate, acetone, methylethylketone, acetonitrile, N,N-dimethylformamide, N,N-dimethylacetamide, dimethylsulfoxide, n-hexane, n-heptane, cyclohexane and mixtures thereof. More preferably, the solvent is toluene. Preferably, the base is added under neat conditions.

The base is preferably added to prevent an increase in the acidity of the reaction mixture, as, during the reaction, the activating agent forms an acid that, in the absence of the base, would acidify the reaction mixture. For example, when the activating agent is trifluoromethanesulfonic anhydride, trifluoromethanesulfonic acid is formed during the reaction, and, when the activating agent is an acyl chloride, such as trifluoromethanesulfonyl chloride, HCl is formed during the reaction. Without the addition of the base, the formation of an acid in the reaction mixture increases the acidity over the course of the reaction, slowing the rate of the reaction, and decomposing the macrocycle. Therefore, the base is preferably added to the reaction mixture to neutralize the acid produced in the process.

Following or with the addition of the base the reaction mixture is combined with the activating conversion reagent, dropwise, in parts, or all at once. Preferably, the progress of the reaction is monitored, e.g., with thin layer chromatography (TLC), until the reaction is complete or nearly complete.

Preferably, the conversion reagent is selected from the group consisting of: fluorosulfonic anhydride, fluorosulfonyl chloride, trifluoromethanesulfonic anhydride, trifluoromethanesulfonyl chloride, methanesulfonic anhydride, methanesulfonyl chloride, phenylmethanesulfonic anhydride, phenylmethanesulfonyl chloride, p-toluenesulfonic anhydride, p-toluenesulfonyl chloride, benzenesulfonic anhydride, and benzenesulfonyl chloride. More preferably, the conversion reagent is selected from the group consisting of: triflouromethanesulfonic anhydride and trifluoromethanesulfonyl chloride. The added conversion reagent may be in solution, where the solvent is selected from the same group of solvents that is used to form the solution with the base, as described above. Preferably, the solvent is selected from the group consisting of: toluene, n-hexane, n-heptane and cyclohexane.

The time required for the complete or near complete conversion of the ascomycin to the corresponding activated ascomycin, such as a ascomycin 32-triflate, can vary somewhat, depending upon the reaction conditions, such as the temperature, and the solvent, base, and activating agent utilized. Those skilled in the art will understand how to monitor the reaction, e.g., by TLC, at appropriate time intervals, depending on the conditions chosen. As a non-limiting example, when trifluoromethanesulfonic anhydride as the activating agent is used, the reaction is almost instantaneous, even at −40° C., provided that the reaction mixture contains a sufficient amount of base, i.e., about 3 to about 4 equivalents. In contrast, for example, with the use of p-toluenesulfonyl chloride as the activating conversion agent, the reaction requires 1 to 3 hours at 0° C. with 3 to 4 equivalents of base, and the reaction may require at least a day with 1 equivalent of base.

After the addition of the activating conversion reagent, the reaction mixture is then combined with a solution of a chloride-ion source. Preferably, the solution of chloride-ion source is added to the reaction mixture. Useful chloride-ion sources include, but are not limited to lithium chloride, sodium chloride, potassium chloride, magnesium chloride, calcium chloride, aluminum chloride, iron(II) chloride, iron (III) chloride, ammonium chloride, hydrochlorides of organic bases, quaternary ammonium chlorides, quaternary phosphonium chlorides, tetrabutylammonium chloride, benzyl-triethylammonium chloride and similar quaternary ammonium chlorides, and hydrochlorides of the bases discussed above. Preferably, chloride-ion source is benzyltriethylammonium chloride. Useful solvents for the chloride-ion source include those discussed above for the base and activating agent. Alternatively, the chloride-ion source can be added to the reaction mixture neat.

After the addition of the chloride-ion source the reaction mixture is stirred at a temperature above about 0° C., but below the reflux temperature of the solvent or mixture of solvents used in the reaction mixture. Preferably, the temperature is at least about 25° C. Again, the progress of the reaction is monitored to determine completion, such as with TLC.

The time required for the disappearance of the intermediate activated ascomycin derivative, such as 32-triflate, will vary somewhat depending on the precise conditions used, and depends mainly on the reaction temperature and the solubility of the selected chloride-ion source. Typically, the time is between about 1 hour and 1 day at room temperature. At a lower temperature and/or with a chloride-ion source having a lower solubility, the reaction is significantly slower. Longer reactions are less favored, as the possibility of the formation of undesirable side products is increased.

The pimecrolimus recovering step comprises: adding water with a water immiscible organic solvent to obtain a two phase system; separating the two phase system; extracting the organic phase with an aqueous $KHSO_4$ solution, $NaHCO_3$ solution and brine, concentrating the organic phase; and drying.

Alternatively, the recovering step comprises: adding water to the reaction mixture to obtain a two phase system; separating the two phase system; and concentrating the organic phase.

The crude product is obtained as an amorphous solid by employing high vacuum during the last part of the concentration process.

Preferably, the crude product is purified by column chromatography prior to the drying step. The solution containing the crude product is concentrated and subjected to chromatography column. After the chromatography, the pure fractions are combined and concentrated to obtain an amorphous solid.

Preferably, the pimecrolimus obtained after the purification step has a purity of at least about 95% area by HPLC, more preferably of at least about 98% area by HPLC.

In one embodiment, the present invention comprises pimecrolimus having a purity of at least about 95% area by HPLC, more preferably of at least about 98% area by HPLC.

Another embodiment of the present invention is a pharmaceutical formulation comprising a therapeutically effective amount of the above purified Pimecrolimus, and an amount of pharmaceutically acceptable excipient.

"Therapeutically effective amount" means the amount of the purified pimecrolimus, when administered to a patient for treating a disease or other undesirable medical condition, is sufficient to have a beneficial effect with respect to that disease or condition. The "therapeutically effective amount" will vary depending on the purity, the disease or condition and its severity, and the age, weight, etc., of the patient to be treated. Determining the therapeutically effective amount of a given pure pimecrolimus is within the ordinary skill of the art, and requires no more than routine experimentation.

Another embodiment of the present invention is a method for treating a patient suffering from Atopic dermatitis, comprising the step of administering to the patient the pharmaceutical formulation comprising a therapeutically effective amount of purified Pimecrolimus produced by the present invention. A further embodiment of the present invention is a method of providing immunosuppression to a patient in need thereof comprising the step of administering to the patient the pharmaceutical formulation comprising a therapeutically effective amount of purified Pimecrolimus produced by the present invention.

Pharmaceutical formulations of the present invention contain the purified Pimecrolimus produced by the processes of the present invention. In addition to the active ingredient(s), the pharmaceutical formulations of the present invention may contain one or more excipients. Excipients are added to the formulation for a variety of purposes.

Diluents may be added to the formulations of the present invention. Diluents increase the bulk of a solid pharmaceutical composition, and may make a pharmaceutical dosage form containing the composition easier for the patient and caregiver to handle. Diluents for solid compositions include, for example, microcrystalline cellulose (e.g., AVICEL®), microfine cellulose, lactose, starch, pregelatinized starch, calcium carbonate, calcium sulfate, sugar, dextrates, dextrin, dextrose, dibasic calcium phosphate dihydrate, tribasic calcium phosphate, kaolin, magnesium carbonate, magnesium oxide, maltodextrin, mannitol, polymethacrylates (e.g., EUDRAGIT®), potassium chloride, powdered cellulose, sodium chloride, sorbitol, and talc.

Solid pharmaceutical compositions that are compacted into a dosage form, such as a tablet, may include excipients whose functions include helping to bind the active ingredient and other excipients together after compression. Binders for solid pharmaceutical compositions include acacia, alginic acid, carbomer (e.g., carbopol), carboxymethylcellulose sodium, dextrin, ethyl cellulose, gelatin, guar gum, hydrogenated vegetable oil, hydroxyethyl cellulose, hydroxypropyl cellulose (e.g., KLUCEL®), hydroxypropyl methyl cellulose (e.g., METHOCEL®), liquid glucose, magnesium aluminum silicate, maltodextrin, methylcellulose, polymethacrylates, povidone (e.g., KOLLIDON®, PLASDONE®), pregelatinized starch, sodium alginate, and starch.

The dissolution rate of a compacted solid pharmaceutical composition in the patient's stomach may be increased by the addition of a disintegrant to the composition. Disintegrants include alginic acid, carboxymethylcellulose calcium, carboxymethylcellulose sodium (e.g., AC-DI-SOL®, PRIMELLOSE®), colloidal silicon dioxide, croscarmellose sodium, crospovidone (e.g., KOLLIDON®, POLYPLASDONE®), guar gum, magnesium aluminum silicate, methyl cellulose, microcrystalline cellulose, polacrilin potassium, powdered cellulose, pregelatinized starch, sodium alginate, sodium starch glycolate (e.g., EXPLOTAB®), and starch.

Glidants can be added to improve the flowability of a non-compacted solid composition, and to improve the accuracy of dosing. Excipients that may function as glidants include colloidal silicon dioxide, magnesium trisilicate, powdered cellulose, starch, talc, and tribasic calcium phosphate.

When a dosage form such as a tablet is made by the compaction of a powdered composition, the composition is subjected to pressure from a punch and dye. Some excipients and active ingredients have a tendency to adhere to the surfaces of the punch and dye, which can cause the product to have pitting and other surface irregularities. A lubricant can be added to the composition to reduce adhesion, and ease the release of the product from the dye. Lubricants include magnesium stearate, calcium stearate, glyceryl monostearate, glyceryl palmitostearate, hydrogenated castor oil, hydrogenated vegetable oil, mineral oil, polyethylene glycol, sodium benzoate, sodium lauryl sulfate, sodium stearyl fumarate, stearic acid, talc, and zinc stearate.

Flavoring agents and flavor enhancers make the dosage form more palatable to the patient. Common flavoring agents and flavor enhancers for pharmaceutical products that may be included in the composition of the present invention include maltol, vanillin, ethyl vanillin, menthol, citric acid, fumaric acid, ethyl maltol, and tartaric acid.

Solid and liquid compositions may also be dyed using any pharmaceutically acceptable colorant to improve their appearance, and/or facilitate patient identification of the product and unit dosage level.

In liquid pharmaceutical compositions prepared using purified Pimecrolimus produced by the processes of the present invention, Pimecrolimus and any other solid excipients are dissolved or suspended in a liquid carrier such as water, vegetable oil, alcohol, polyethylene glycol, propylene glycol or glycerin.

Liquid pharmaceutical compositions may contain emulsifying agents to disperse uniformly throughout the composition an active ingredient or other excipient that is not soluble in the liquid carrier. Emulsifying agents that may be useful in liquid compositions of the present invention include, for example, gelatin, egg yolk, casein, cholesterol, acacia, tragacanth, chondrus, pectin, methyl cellulose, carbomer, cetostearyl alcohol, and cetyl alcohol.

Liquid pharmaceutical compositions may also contain a viscosity enhancing agent to improve the mouth-feel of the product and/or coat the lining of the gastrointestinal tract. Such agents include acacia, alginic acid bentonite, carbomer, carboxymethylcellulose calcium or sodium, cetostearyl alcohol, methyl cellulose, ethylcellulose, gelatin guar gum, hydroxyethyl cellulose, hydroxypropyl cellulose, hydroxypropyl methyl cellulose, maltodextrin, polyvinyl alcohol, povidone, propylene carbonate, propylene glycol alginate, sodium alginate, sodium starch glycolate, starch tragacanth, and xanthan gum.

Sweetening agents such as sorbitol, saccharin, sodium saccharin, sucrose, aspartame, fructose, mannitol, and invert sugar may be added to improve the taste.

Preservatives and chelating agents such as alcohol, sodium benzoate, butylated hydroxyl toluene, butylated hydroxyanisole, and ethylenediamine tetraacetic acid may be added at levels safe for ingestion to improve storage stability.

A liquid composition may also contain a buffer such as guconic acid, lactic acid, citric acid or acetic acid, sodium guconate, sodium lactate, sodium citrate, or sodium acetate. Selection of excipients and the amounts used may be readily determined by the formulation scientist based upon experience and consideration of standard procedures and reference works in the field.

The solid compositions of the present invention include powders, granulates, aggregates and compacted compositions. The dosages include dosages suitable for oral, buccal, rectal, parenteral (including subcutaneous, intramuscular, and intravenous), inhalant, and ophthalmic administration. Although the most suitable administration in any given case will depend on the nature and severity of the condition being treated, the most preferred route of the present invention is oral. The dosages may be conveniently presented in unit dosage form, and prepared by any of the methods well-known in the pharmaceutical arts.

Dosage forms include solid dosage forms like tablets, powders, capsules, suppositories, sachets, troches, and lozenges, as well as liquid syrups, suspensions, and elixirs.

The oral dosage form of the present invention is preferably in the form of an oral capsule having a dosage of about 10 mg to about 160 mg, more preferably from about 20 mg to about 80 mg, and most preferably capsules of 20, 40, 60, and 80 mg. Daily dosages may include 1, 2, or more capsules per day.

The dosage form of the present invention may be a capsule containing the composition, preferably a powdered or granulated solid composition of the invention, within either a hard or soft shell. The shell may be made from gelatin, and, optionally, contain a plasticizer such as glycerin and sorbitol, and an opacifying agent or colorant.

A composition for tableting or capsule filling may be prepared by wet granulation. In wet granulation, some or all of the active ingredients and excipients in powder form are blended, and then further mixed in the presence of a liquid, typically water, that causes the powders to clump into granules. The granulate is screened and/or milled, dried, and then screened and/or milled to the desired particle size. The granulate may then be tableted, or other excipients may be added prior to tableting, such as a glidant and/or a lubricant.

A tableting composition may be prepared conventionally by dry blending. For example, the blended composition of the actives and excipients may be compacted into a slug or a sheet, and then comminuted into compacted granules. The compacted granules may subsequently be compressed into a tablet.

As an alternative to dry granulation, a blended composition may be compressed directly into a compacted dosage form using direct compression techniques. Direct compression produces a more uniform tablet without granules. Excipients that are particularly well suited for direct compression tableting include microcrystalline cellulose, spray dried lactose, dicalcium phosphate dihydrate, and colloidal silica. The proper use of these and other excipients in direct compression tableting is known to those in the art with experience and skill in particular formulation challenges of direct compression tableting.

A capsule filling of the present invention may comprise any of the aforementioned blends and granulates that were described with reference to tableting, however, they are not subjected to a final tableting step.

The active ingredient and excipients may be formulated into compositions and dosage forms according to methods known in the art.

Having described the invention with reference to certain preferred embodiments, other embodiments will become apparent to one skilled in the art from consideration of the specification. The invention is further defined by reference to the following examples describing in detail the preparation of the composition and methods of use of the invention. It will be apparent to those skilled in the art that many modifications, both to materials and methods, may be practiced without departing from the scope of the invention.

Instruments

| Chromatography method for measuring purity: | |
| --- | --- |
| Eluent: | n-Hexane:acetone:acetonitrile 20:2:1 (by volume) |
| Flow: | 20-40 mL/min |
| Detection: | TLC (UV, 254 nm) |
| Sample conc: | 400-500 g/L |
| Sample vol: | 60-70 mL |
| Column temp: | 25° C. |
| Detection limit: | not determined |

EXAMPLES

The following non-limiting examples are merely illustrative of the preferred embodiments of the present invention, and are not to be construed as limiting the invention, the scope of which is defined by the appended claims.

Example 1

A 3.0 g sample of crude ascomycin was purified by passing it through a short silica column. The 3.0 g of syrup obtained was dissolved in 25 ml of anhydrous dichloromethane. The solution was cooled to −15° C. with a slow stream of dried nitrogen gas bubbling through the solution.

A 5 percent by weight solution of trifluoromethanesulfonic anhydride in anhydrous dichloromethane was added to the above solution in 6 ml parts, together with 0.3 g parts of 2,6-lutidine. After the addition of a total of 24 ml trifluoromethanesulfonic anhydride solution, 28 g of a 10 percent by weight lithium chloride solution was added to the reaction mixture, and the reaction mixture was allowed to warm to room temperature, i.e., about 21° C. The reaction mixture was then stirred for 4 days.

The reaction mixture was diluted with a mixture of 200 ml ethyl acetate and 25 ml of water, and poured into a separating funnel, and shaken. After extraction, 25 ml of a 10 percent by weight aqueous solution of $KHSO_4$ was added. Following additional shaking, the aqueous layer was removed, and the organic phase was washed three times with 25 ml of a 10 percent by weight aqueous $KHSO_4$ solution, twice with 25 ml of a saturated aqueous $NaHCO_3$ solution, and twice with 25 ml of brine. The organic phase was dried over anhydrous $MgSO_4$. After filtration, it was concentrated in vacuum, and, then, finally, under high vacuum to completely remove the solvent. The yield was 2.94 g of crude amorphous pimecrolimus.

The product was purified by flash chromatography using n-hexane/acetone (2:1, V/V) as an eluent. The yield was 2.54 g of amorphous pimecrolimus.

Example 2

A 31.4 gram sample of ascomycin, assayed at 92.7 percent, was dissolved in 200 ml of toluene. The solution was concentrated at 40° C. to dryness (syrup). Anhydrous toluene was added to provide a 230 g solution, and 275 ml of anhydrous acetonitrile was then added. The solution was cooled to a jacket temperature of −15° C. with a slow stream of dried nitrogen over the surface of the solution. Simultaneously, 315 ml of anhydrous toluene was cooled in a smaller reactor, having a jacket temperature of −15° C., also with a slow stream of dried nitrogen over the surface of the liquid. When the temperature of the toluene reached about −12.5° C., 13.85 g of trifluoromethanesulfonic anhydride (triflic anhydride) was added dropwise. At about the same time, 11.33 g of ethyldiisopropylamine (EDIPA) was added dropwise to the ascomycin solution. After a few minutes, the triflic anhydride solution was transferred to the ascomycin solution. When the addition was complete, the temperature of the jacket was set to 26° C. When the temperature of the reaction mass reached about 0° C., 300 g of a 12.5 percent by weight solution of benzyl-triethylammonium chloride ("$BnEt_3NCl$") in anhydrous acetonitrile was added. Water in an amount of 200 ml was added 45 minutes after the temperature of the reaction mass reached about 24° to about 25° C. Following a period of vigorous stirring, the aqueous phase was removed, and an additional 200 ml of water was added, and, again, removed after mixing. The organic phase was concentrated at 40° C. until almost all of the acetonitrile was removed. The solution was diluted with the same volume of toluene with stirring. The precipitating solids were filtered, and washed with toluene. The filtrate was concentrated to dryness at 40° C. Crude amorphous pimecrolimus was obtained as a brownish foam with a yield of 33 g.

Example 3

30 g ascomycin was converted to crude Pimecrolimus according to Example 2. The crude product was introduced to a column of 600 g silica gel 60 (0.040-0.063 mm) as a concentrated solution in toluene. This was eluted with n-hexane-acetone-acetonitrile (20:2:1) mixture.

The fractions that contained Pimecrolimus of sufficient purity according to analysis by HPLC are combined and extracted with 10 V/V % acetonitrile. The lower phase, that contains the solution of Pimecrolimus in a mixture of acetonitrile and acetone (with some n-hexane), was removed and the upper phase (mainly n-hexane) was extracted twice with 5 V/V % acetonitrile. The lower (acetonitrile-acetone) phases were combined and concentrated at 40° C. to obtain a colorless resin. This was then dissolved in 217 ml acetone at 40° C. and concentrated. Residue: 38.76 g. The residue was diluted with 6 ml distilled water with stirring. Finally 1 ml acetone was added. This solution was added slowly to 2 L chilled distilled water which was stirred efficiently. After the addition had been completed, the suspension was stirred 20 min at 0° C. Then the solid was filtered and dried at 45° C. in vacuum oven overnight. Product: 15.65 g yellowish solid. Amorphous (XRD, DSC). Purity: 95.75% area by HPLC.

While it is apparent that the invention disclosed herein is well calculated to fulfill the objects stated above, it will be appreciated that numerous modifications and embodiments may be devised by those skilled in the art. Therefore, it is intended that the appended claims cover all such modifications and embodiments as falling within the true spirit and scope of the present invention.

What is claimed:

1. A process for preparing pimecrolimus comprising:
  a) dissolving ascomycin in an organic solvent;
  b) activating ascomycin at C-32 by combining ascomycin with an organic or inorganic base and a conversion reagent to obtain an activated ascomycin derivative, wherein the conversion agent is selected from the group consisting of fluorosulfonic anhydride, fluorosulfonyl chloride, trifluoromnethanesulfonic anhydride, trifluoromethanesulfonyl chloride, methanesulfonic anhydride, methanesulfonyl chloride, phenylmethanesulfonic anhydride, phenylmethanesulfonyl chloride, p-toluenesulfonic anhydride, p-toluenesulfonyl chloride, benzenesulfonic anhydride, and benzenesulfonyl chloride;
  c) reacting the activated derivative of ascomycin with a chloride ion source to obtain pimecrolimus; and
  d) recovering the obtained pimecrolimus.

2. The process of claim 1, wherein the organic solvent is selected from the group consisting of: dichloromethane, chloroform, diethylether, diisopropylether, methyl-t-butylether, toluene, ethyl acetate, i-butylacetate, acetone, methylethylketone, acetonitrile, N,N-dimethylformaxnide, N,N-dimethylacetamide, dimethylsulfoxide, and mixtures thereof.

3. The process of claim 2, wherein the organic solvent is toluene, acetonitrile or mixtures thereof.

4. The process of claim 1, wherein the ascomycin is dissolved in an organic solvent at a temperature of at least about 25° C.

5. The process of claim 1, wherein the obtained ascomycin solution is stirred at a temperature of less than about 25° C.

6. The process of claim 5, wherein the obtained ascomycin solution is stirred at a temperature less than 0° C.

7. The process of claim 6, wherein the obtained ascomycin solution is stirred at a temperature less than −20° C.

8. The process of claim 1, wherein the base is in an amount of about 1 to about 4 equivalents.

9. The process of claim 1, wherein the base in step (b) is added dropwise, in parts or all at once.

10. The process of claim 1, wherein the base is selected from the group consisting of: triethylamine, diisopropyl-ethylamine (EDIPA), N-methyl-morpholine, N,N-dimethylaniline, pyridine, and substituted pyridine derivatives.

11. The process of claim 10, wherein the base is selected from the group consisting of diisopropyl-ethylamine (EDIPA), s-collidine and 2,6-lutidine.

12. The process of claim 1, wherein the base is added in a solution that contains a solvent selected from the group consisting of: dichloromethane, chloroform, diethylether, diisopropylether, methyl-t-butylether, toluene, ethyl acetate, i-butylacetate, acetone, methylethylketone, acetonitrile, N,N-dimethylformamide, N,N-dimethylacetamide, dimethylsulfoxide, n-hexane, n-heptane, cyclohexane and mixtures thereof.

13. The process of claim 12, wherein the base is added in a solution that contains toluene.

14. The process of claim 1, wherein the activated ascomycin derivative is selected from the group consisting of: sulfonate ester, tosylate or mesylate and triflate.

15. The process of claim 1, wherein the conversion reagent is selected from the group consisting of: trifluoromethanesulfonic anhydride and trifluoromethanesulfonyl chloride.

16. The process of claim 1, wherein the conversion reagent is added in a solution that contains a solvent selected from the group consisting of: dichloromethane, chloroform, diethylether, diisopropylether, methyl-t-butylether, toluene, ethyl acetate, i-butylacetate, acetone, methylethylketone, acetonitrile, N,N-dimethylformamide, N,N-dimethylacetamide, dimethylsulfoxide, n-hexane, n-heptane, cyclohexane and mixtures thereof.

17. The process of claim 16, wherein the conversion reagent is added in a solution that contains a solvent selected from the group consisting of: toluene, n-hexane, n-heptane and cyclohexane.

18. The process of claim 1, wherein the chloride ion source in step c) is selected from the group consisting of: lithium chloride, sodium chloride, potassium chloride, magnesium chloride, calcium chloride, aluminum chloride, iron (II) chloride, iron(III) chloride, ammonium chloride, hydrochlorides of organic bases, quarternary ammonium chlorides, quarternary phosphonium chlorides, tetrabutylammonium chloride, benzyl-triethylammonium chloride and similar quarternary ammonium chlorides, and hydrochlorides of the bases selected from the group consisting of: triethylamine, diisopropyl-ethylamine (EDIPA), N-methyl-morpholine, N,N-dimethylaniline, pyridine, and substituted pyridine derivatives.

19. The process of claim 18, wherein the chloride-ion source is benzyltriethylammonium chloride.

20. The process of claim 1, wherein the chloride ion source is added in a solution that contains a solvent selected from the group consisting of: dichloromethane, chloroform, diethylether, diisopropylether, methyl-t-butylether, toluene, ethyl acetate, i-butylacetate, acetone, methylethylketone, acetonitrile, N,N-dimethylformamide, N,N-dimethylacetamide, dimethylsulfoxide, n-hexane, n-heptane, cyclohexane and mixtures thereof.

21. The process of claim 1, further comprising stirring the reaction mixture prior to step d).

22. The process of claim 1, wherein the recovering step comprises:
adding water with a water immiscible organic solvent to obtain a two phase system;
separating the two phase system; extracting the organic phase with an aqueous $KHSO_4$ solution, $NaHCO_3$ solution and brine, concentrating the organic phase; and drying.

23. The process of claim 1, wherein the recovering step comprises:
adding water to the reaction mixture to obtain a two phase system; separating the two phase system; and concentrating the organic phase.

24. The process of claim 1, further comprising purifying the obtained pimecrolimus by column chromatography to obtain a purified pimecrolimus.

25. The process of claim 24, wherein the purified pimecrolimus has a purity of at least about 95% area by HPLC.

26. The process of claim 25, wherein the purified pimecrolimus has a purity of at least about 98% area by HPLC.

27. The process of claim 10, wherein the substituted pyridine derivative is selected from the group consisting of 2,6-lutidine, s-collidine, and 4 dimethylaminopyridine.

28. The process of claim 18, wherein the substituted pyridine derivative is selected from the group consisting of 2,6-lutidine, s-collidine, and 4 dimethylaminopyridine.

* * * * *

UNITED STATES PATENT AND TRADEMARK OFFICE
CERTIFICATE OF CORRECTION

PATENT NO. : 7,279,571 B2
APPLICATION NO. : 11/293353
DATED : October 9, 2007
INVENTOR(S) : Gyollai et al.

It is certified that error appears in the above-identified patent and that said Letters Patent is hereby corrected as shown below:

Column 1
Line 18, change "pure" to --purify--

Column 3
Lines 52-53, change "diisopropyl-ethy-lamine" to --diisopropyl-ethyl-amine--

Column 9
Line 61, change "reaction mass" to --reaction mixture--

Column 11
Lines 14-15, change "N,N-dimethy-laniline" to --N,N-dimethyl-aniline--
Lines 33-34, change "trif-louromethanesulfonic" to --tri-fluoromethanesulfonic--
Lines 34-35, change "trifluoromethanesulfo-nyl" to --trifluoromethanesul-fonyl--

Column 12
Line 45, change "4 dimethylaminopyridine" to --4-dimethylaminopyridine--
Line 48, change "4 dimethylaminopyridine" to --4-dimethylaminopyridine--

Signed and Sealed this

Third Day of February, 2009

JOHN DOLL
*Acting Director of the United States Patent and Trademark Office*